United States Patent [19]

Hardy et al.

[11] Patent Number: 4,540,682

[45] Date of Patent: Sep. 10, 1985

[54] PHARMACEUTICAL PEPTIDES, PREPARATION, USE AND INTERMEDIATES

[75] Inventors: George W. Hardy, Biggin Hill; Lawrence A. Lowe, Swanley; Terence W. Smith, Orpington, all of United Kingdom

[73] Assignee: Burroughs Wellcome Co., Triangle Park, N.C.

[21] Appl. No.: 613,868

[22] Filed: May 23, 1984

[30] Foreign Application Priority Data

May 26, 1983 [GB] United Kingdom ................ 8314646

[51] Int. Cl.³ .................... A61K 37/00; C07C 103/52
[52] U.S. Cl. ...................................... 514/18; 514/809; 260/112.5 E
[58] Field of Search ................ 260/172.5 E; 424/177

[56] References Cited

U.S. PATENT DOCUMENTS 4,178,371 12/1979 Morgan ........................ 260/112.5 E

OTHER PUBLICATIONS

Chem. Pharm. Bull. 30, (7) 2447–2452 (1982).

*Primary Examiner*—Delbert R. Phillips
*Attorney, Agent, or Firm*—Donald Brown

[57] ABSTRACT

Novel peptides of formula (I)

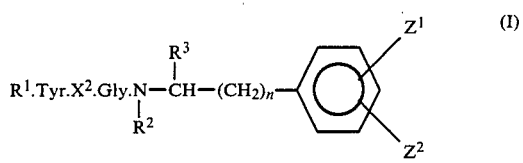

wherein
$R^1$ is hydrogen, alkyl of 1 or 2 carbon atoms or an amidino group,
$R^2$ is alkyl of 1 or 2 carbon atoms,
$R^3$ is hydrogen or carbamyl,
$X^2$ is a D-radical having the structure:

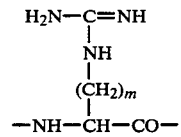

$Z^1$ and $Z^2$ are the same or different and each is hydrogen, halo, nitro or trifluoromethyl and at least one is other than hydrogen,
m is 2, 3 or 4 and
n is 0, 1 or 2,
provided that when $R^3$ is carbamyl then n is always 1; and salts thereof.

The compounds have a selectively peripheral analgesic effect when administered to mammals and also exhibit antidiarrhoeal and antitussive activity and may thus be used in human or veterinary medicine for the relief or prevention of pain, for the treatment of diarrhoea or dysentery and for the suppression of cough.

42 Claims, No Drawings

PHARMACEUTICAL PEPTIDES, PREPARATION, USE AND INTERMEDIATES

This invention relates to peptides useful in human and veterinary medicine, to the preparation of such compounds, to pharmaceutical formulations containing such compounds and the preparation of such formulations, to the use of the compounds in human and veterinary medicine and to intermediates for the said compounds and the preparation thereof.

The present invention more particularly relates to the novel peptides of formula (I)

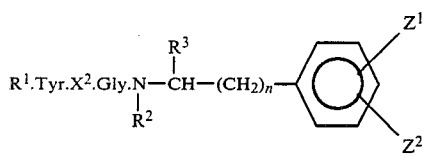

as hereinafter defined which have been found to be of value in human and veterinary medicine in the prevention and relief of pain, that is to say, the said compounds are analgesics.

The safe and effective prevention and relief of pain has for long been the subject of investigation and enquiry and a number of analgesic agents are available to the physician and veterinarian. Such agents are recognised as producing this effect by either or both of two distinguishable mechanisms neither of which is as yet fully understood. One such mechanism, giving rise to so-called central analgesia, is believed to involve receptors in the central nervous system (the brain and spinal cord) whilst the other, giving rise to the phenomenon of peripheral analgesia, is associated with events outside of these structures.

Agents having an effect with at least a substantial centrally-mediated component include morphine, heroin and other of the opioids (see for example Goodman and Gilman's "*The Pharmacological Basis of Therapeutics*", sixth edition (1980), Macmillan Publishing Co., Inc. especially at Chapter 22, pages 494 to 534). Such compounds are valued for their efficacy in severe and often otherwise intractable pain, for example, the pain of terminal illness such as cancer, post-operative pain and pain in parturition. As is well known, however, (loc. cit., Chapter 23, pages 535 to 584) repeated administration of morphine et al. can lead to a physical dependence on the drug and tolerance to its actions and to withdrawal symptoms when administration is discontinued. Research has indicated that these aspects and the further side-effect of depression of respiration, all phenomena of the central nervous system, are intimately linked with analgesic potency.

Currently recognized peripheral analgesics, however, are non-opioid in character.

In 1975 Hughes et al. (Nature, 1975, 255, 577–579) reported the identification of two structurally related pentapeptides from the brain with potent opiate agonist activity, respectively named methionine-enkephalin and leucine-enkephalin. Their properties and those of a large number of their analogues have since been investigated in detail and the picture has emerged of a class of compounds having a pharmacological spectrum very similar to that of the opioids. In particular it has been found that, allied to their analgesic action, the enkephalins have a physical dependence/tolerance potential (Wei, *J.Pharmacol.Exp.Ther.* 216: 12–18, 1981), exhibit cross tolerance with opioids (Waterfield et al., *Nature*, 1976, 260, 624–625) and have a respiratory-depressant effect (Isom et al., *Pharmacologist* 21/3, 198 (1979)).

In direct contrast the analgesia induced by the peptides of formula (I) is sensibly only peripheral in origin. The compounds lack any significant degree of central analgesic activity and are especially advantageous in being without a respiratory—depressant effect and in having only a very low physical dependence/tolerance potential. These advantages and the specificity of action are together believed to be associated with the compounds' inability to cross the blood/brain barrier to any appreciable extent.

In formula (I), as set forth above,
$R^1$ is hydrogen, alkyl of 1 or 2 carbon atoms or an amidino group,
$R^2$ is alkyl of 1 or 2 carbon atoms,
$R^3$ is hydrogen or carbamyl,
$X^2$ is a D-radical having the structure:

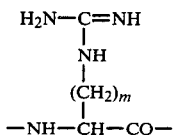

$Z^1$ and $Z^2$ are the same or different and each is hydrogen, halo, nitro or trifluoromethyl and at least one is other than hydrogen,
m is 2, 3 or 4 and
n is 0, 1 or 2,
provided that when $R^3$ is carbamyl then n is always 1; and salts thereof.

Specific identifies for $X^2$ are the following D-radicals: 2-amino-4-guanidinobutyryl (m is 2), arginyl (m is 3) and homoarginyl (m is 4).

The halo identities for $Z^1$ and $Z^2$ may be selected from fluoro, chloro, bromo and iodo.

As subclasses of peptides within formula (I) may be mentioned those wherein:
(i) $R^1$ is an amidino group
(ii) $R^2$ is ethyl
(iii) $R^3$ is hydrogen
(iv) $X^2$ is D-arginyl
(v) one of $Z^1$ and $Z^2$ is hydrogen and other is nitro or fluoro, preferably in the 4-position
(vi) n is 1.

A further class of peptides within formula (I) is that wherein $R^1$ is an amidino group and $R^3$ is carbamyl.

Preferred peptides within formula (I) are:

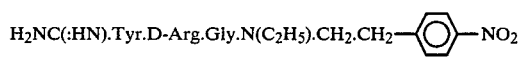

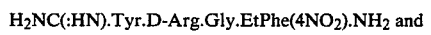

together with salts thereof.

The abbreviations used herein for amino acids and their radicals are those conventional in the art and may be found in, for example, *Biochem. J.* (1972) 126, 773–780. In the above and throughout the following all references are to the L-configuration of chiral amino acids and their radicals, unless otherwise stated.

In the salts of the peptides the biological activity resides in the peptide moiety and the identity of the acid is of less importance although for therapeutic purposes it is preferably pharmacologically acceptable to the recipient. Examples of pharmacologically acceptable acids include mineral acids such as hydrochloric, hydrobromic, phosphoric, metaphosphoric, nitric and sulphuric acids and organic acids such as tartaric, acetic, citric, malic, lactic, fumaric, benzoic, glycollic, gluconic, gulonic, succinic and arylsulphonic, for example p-toluenesulphonic, acids. The pharmacologically acceptable salts together with those salts which are not thus acceptable have utility in the isolation and/or the purification of the free peptides and of course the unacceptable salts are also valuable in being convertible to the acceptable salts by techniques well known in the art.

The analgesic properties of the peptides of formula (I) and in particular the selectively peripheral site of action thereof have been demonstrated by means of the following investigations.

(1) Both the hotplate test (Woolfe and MacDonald, *J. Pharmacol. Exp. Ther.* 80: 300, 1944) and the irritant-induced writhing (stretch) test (Vander Wende and Margolin, *Fed. Proc.* 15: 494, 1956) are standard in the art for the investigation of analgesic activity. Whereas it is believed that the pain in the latter can be ameliorated either centrally or peripherally, it is thought that that induced in the hotplate test is affected only at the central level. When tested by modifications of these literature procedures the peptides are considerably more potent in the writhing test than in the hotplate test on parenteral (i.e. peripheral) administration, that is to say a lower dose of the compound is required to provide a given reduction in the reaction to the test stimulus, indicating a peripheral site of action.

(2) The respective time courses of the analgesia induced by the peptides in the hotplate and writhing tests, upon peripheral (parenteral) administration, indicate that the compounds penetrate the blood/brain barrier comparatively slowly and to only a very limited extent.

(3) The analgesia induced by the peptides in the writhing test upon peripheral (parenteral) administration is antagonised by parenteral administration of the quaternary opioid antagonist N-allyl-normorphine methiodide (N-methylnalorphine; Koczka et al., *Acta Chim. Acad. Sci. Hung.* 51: 393, 1967), i.e. a higher dose of the peptide is required in the presence than in the absence of the opioid for the same effect. As penetration of the blood/brain barrier by the quaternary compound is minimal (c.f. Tavani et al., *European J. Pharmacol.* 59: 151–154, 1979) both the peptide—induced analgesia and the antagonism thereof are effected at the peripheral level.

In addition to the analgesic properties hereinabove described the peptides of formula (I) and their salts have been found to exhibit (a) antidiarrhoeal and (b) antitussive activity when investigated according to standard pharmacological procedures.

The peptides of formula (I) and the salts thereof may be prepared by those methods known in the art for the synthesis of compounds of analogous structure and in this regard reference is made, by way of illustration only, to the following literature.

(a) Schroder and Luebke, *"The Peptides"* (Academic Press, 1965).

(b) Stewart and Young, *"Solid Phase Peptide Synthesis"* (W H Freeman and Co., 1969).

(c) Bellean and Malek, *J. Am. Chem. Soc.* 90: 165, 1968.

(d) Beyerman, *Helv. Chim. Acta* 56: 1729, 1973.

(e) Tilak, *Tetrahedron Letters* 849 (1970).

(f) *"Methoden der Organischen Chemie"* (Houben-Weyl), Vol. 15, *"Synthese von Peptiden"*, Parts 1 and 2 (Georg Thieme Verlag, 1974).

(g) *"The Peptides: Analysis, Synthesis, Biology"*, Gross, E. and Meinhofer, J. ed., Vols. 1 to 4 (Academic Prekss, 1979).

(h) *"Peptides: Syntheses, Physical Data"*, Voelter, W. and Schmid-Siegmann, E., Vols. 1 to 6 (Georg Thieme Verlag, 1983).

(i) Atherton, E. et al., *Bioorganic Chem.* 8, 351–370 (1979).

(j) Sheppard, R. C., *Chemistry in Britian*, 402–414 (1983).

(k) Atherton, E. et al., *J.C.S. Chem. Comm.*, 1151–1152 (1981).

All references identified hereinabove or in the following are hereby incorporated herein by reference thereto.

(1) In one such preparative approach the peptides and salts are formed by the sequential coupling of appropriate amino acids using either classical methods of peptide synthesis or solid phase procedures, or by the initial preparation and subsequent coupling of peptide subunits. Such reactions may be effected by, for example, activating the reacting carboxyl group of the ingoing amino acid and protecting the non-reacting amino and carboxyl groups, and details of suitable activating and protecting (masking) groups and of suitable reaction conditions (both for the coupling reactions and for the removal of protecting groups) giving the minimum of racemisation may be found in the above-referenced literature.

The peptides and salts may thus be prepared by reacting a reagent (II)

$$R^1-Y^1-OH \qquad (II)$$

wherein $R^1$ has the meaning as recited in formula (I) and $Y^1$ is a partial radical sequence identical with the corresponding N-terminal partial radical sequence in formula (I), with a reagent (III)

$$H-Y^2 \qquad (III)$$

wherein $Y^2$ is identical with the balance of the above-defined product peptide and includes the corresponding C-terminal partial radical sequence thereof, the reagents (II) and (III) being optionally protected and/or activated where and as appropriate; followed as appropriate by deprotection of the product.

(2) In a further synthetic approach the final step comprises amidation of the corresponding C-terminal peptide carboxylic acid or an appropriate reactive derivative thereof.

The peptides wherein $R^3$ is carbamyl may thus be prepared by, for example, reacting with ammonia a peptide ester (IV)

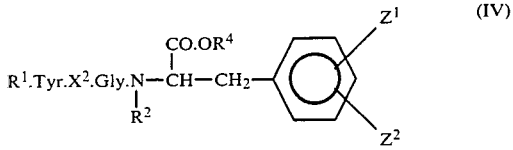

wherein $R^1, R^2, X^2, Z^1$ and $Z^2$ have the meanings as recited in formula (I) and $-OR^4$ is a suitable, displaceable alkoxy, aralkoxy or aryloxy group, for example alkoxy of 1 to 4 carbon atoms (i.e. methoxy, ethoxy, propoxy or butoxy) or benzyloxy. Many such reactive groups are known in the peptide art.

The peptides wherein $R^3$ is hydrogen may be analogously prepared by, for example, reaction of a peptide carboxylic acid (V) or a reactive derivative thereof with an amine (VI)

$$R^1.Tyr.X^2.Gly.OH \qquad (V)$$

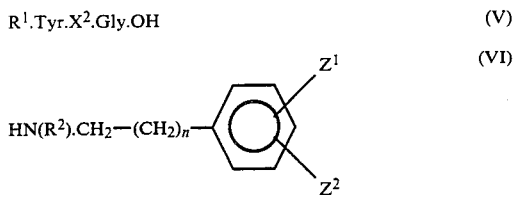

wherein $R^1, R^2, X^2, Z^1, Z^2$ and n have the meanings as recited in formula (I); it will be appreciated that this may, if desired, be effected under conditions and using reagents and procedures (including protection of the N-terminus of (V)) appropriate to peptide coupling techniques, vide(1) supra.

(3) The peptides and salts may also be prepared by the amidination, using 1-amidino-3,5-dimethylpyrazole or a chemically equivalent reagent, of a corresponding peptide wherein $X^2$ is a D-radical having the structure

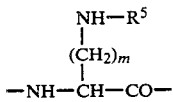

where m has the meaning as recited in formula (I) and $R^5$ is hydrogen or an amidino group, provided that at least one of $R^1$ and $R^5$ is hydrogen.

The D-arginyl and D-homoarginyl peptides may thus be prepared from the corresponding D-ornithyl and D-lysyl compounds, respectively, while the D-(2-amino-4-guanidinobutyryl) peptides result from the corresponding D-(2,4-diaminobutyryl) compounds.

It will be appreciated that when in the corresponding peptide reagent both $R^1$ and $R^5$ are hydrogen and the hydrogen identity for $R^1$ is to be retained in the end product of formula (I), then protection of the peptide N-terminus during the amidination step will be necessary. Details of suitable protecting groups and of conditions for their removal, after the amidination has taken place, are to be found in the previously referenced literature.

The esters (IV), the carboxylic acids (V) and the corresponding D-ornithyl, D-lysyl and D-(2,4-diaminobutyryl) peptides may themselves be prepared by standard techniques analogous to those described under(1) supra.

The peptides of formula (I) may be isolated as the free peptides or as salts thereof and it will be appreciated that the said peptides may be converted to salts thereof, and the reverse, and the salts converted to other salts, by techniques well-known and conventional in the art.

The peptides of formula (I) and the pharmacologically acceptable salts thereof may be used in both human and veterinary medicine for the treatment of diarrhoea and dysentery, for the suppression of cough and for the prevention and relief of pain. Specific indications in the last-named area, by way of example only, include pain arising from soft tissue injury, pain in the post-surgical period, pain in parturition and post-partum, pain in dysmenorrhoea, neuralgia, myalgia, pain in arthritis and rheumatic conditions and that of musculo-skeletal conditions in general.

The peptides and salts may be administered to the human or non-human recipient by a route selected from oral, parenteral (including subcutaneous, intradermal, intramuscular and intravenous), rectal and topical (including dermal, buccal and sublingual). The size of an effective dose of a compound will depend on a number of factors including the identity of the recipient, the condition involved and its severity and the route of administration and will ultimately be at the discretion of the attendant physician or veterinarian although, in view of the subjective nature of the desired end result, self-administration by a human recipient may be acceptable in some circumstances.

For each of the above-recited indications, however, an effective dose for a human being will generally be in the range 0.5 to 50 mg., more generally in the range 1 to 25 mg. and most often in the range 2 to 12.5 mg., a particularly suitable dose being 5 mg. (all doses calculated as the free peptide: for salts the figures would be adjusted proportionately). Administration of such doses may be repeated as required throughout the day, for example, three or four times a day. For veterinary use, for example, in the treatment of non-human mammals such as cats, dogs, cattle, sheep, pigs and horses, and above-recited doses would be increased or decreased at the discretion of the veterinarian having regard to the weight and identity of the recipient.

While it is possible for the compounds to be administered as the raw chemical it is preferable to present them as a pharmaceutical formulation preparation. The formulations of the present invention comprise a peptide of formula (I), as above defined, or a pharmacologically acceptable salt thereof together with one or more acceptable carriers therefor and optionally other therapeutic ingredients. The carrier(s) must be 'acceptable' in the sense of being compatible with the other ingredients of the formulation and not deleterious to the recipient thereof.

The formulations include those suitable for oral, parenteral (including subcutaneous, intradermal, intramuscular and intravenous), rectal and topical (including dermal, buccal and sublingual) administration, although the most suitable route may depend upon, for example, the condition and identity of the recipient. The formulations may conveniently be presented in unit dosage form and may be prepared by any of the methods well-known in the art of pharmacy. All methods include the step of bringing into association the peptide or salt (the active ingredient) with the carrier which constitutes one or more accessory ingredients. In general, the formulations are prepared by uniformly and intimately bringing into association the active ingredient with liquid carriers or finely divided solid carriers or both and then, if appropriate, shaping the product into the desired formulation.

Formulations of the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Formulations for rectal administration may be presented as a suppository with the usual carriers such as cocoa butter, polyethylene glycol or hard fat.

Formulations for topical administration in the mouth, for example buccally or sublingually, include lozenges comprising the active ingredient in aa flavoured basis such as sucrose and acacia or tragacanth, and pastilles comprising the active ingredient in a basis such as gelatin and glycerin or sucrose and acacia.

Preferred unit dosage formulations are those containing an effective dose, as hereinabove recited, or an appropriate fraction thereof, of the active ingredient.

Formulations for topical administration to the skin, i.e. dermally, may be presented in anhydrous forms such as ointments, lotions, pastes, jellies, sprays, aerosols and bath oils. The term ointment includes formulations (including creams) having oleaginous, absorption, water-soluble and emulsion type bases, for example, petrolatum, lanolin, polyethylene glycols and mixtures thereof. Such formulations are particularly valuable for use in the prevention and relief of localised pain, for example that arising in arthritis and rheumatic conditions, and may be applied to the desired area one or more times daily as required; they conveniently contain the compound in a concentration in the range 0.05 to 2% w/w, preferably in the range 0.1 to 1% w/w and most preferably in the range 0.2 to 0.5% w/w, calculated as the free peptide.

It should be understood that in addition to the ingredients particularly mentioned above the formulations of this invention may include other agents conventional in the art having regard to the type of formulation in question, for example, those suitable for oral administration may include flavouring agents.

It will be understood from the foregoing description that this invention may comprise any novel feature described herein, principally but not exclusively, for example:

(a) Peptides of formula (I) as hereinbefore defined and salts thereof.

(b) Methods as hereinbefore described for the preparation of compounds according to (a) supra, together with the compounds when so prepared.

(c) Peptides of formula (I) as hereinbefore defined and pharmacologically acceptable salts thereof, for use in the medical treatment of a mammal, for example, a human being.

(d) Peptides of formula (I) as hereinbefore defined and pharmacologically acceptable salts thereof, for use as an analgesic agent.

(e) Peptides of formula (I) as hereinbefore defined and pharmacologically acceptable salts thereof, for use as an antidiarrhoeal, antidysentery or antitussive agent.

(f) A pharmaceutical formulation comprising a peptide of formula (I) as hereinbefore defined or a pharmacologically acceptable salt thereof together with an acceptable carrier therefor.

(g) A method for the relief or prevention of pain in a mammal, for example, a human being, comprising administering to said mammal a non-toxic, analgesic amount of a peptide of formula (I) as hereinbefore defined or a pharmacologically acceptable salt thereof.

(h) A method for the treatment of diarrhoea or dysentery or for the suppression of cough in a mammal, for example, a human being, comprising administering to said mammal a non-toxic, effective amount of a peptide of formula (I) as hereinbefore defined or a pharmacologically acceptable salt thereof.

(i) Novel compounds of formulae (II) to (VI) as hereinfore defined, methods for their preparation as hereinbefore described and the compounds when so prepared.

The following Examples are provided in illustration of the present invention and should not be construed as in any way constituting a limitation thereof. All temperatures are in degrees Celsius.

EXPERIMENTAL

Abbreviations

DMF: dimethylformamide
THF: tetrahydrofuran
DCCl: dicyclohexylcarbodiimide
HOBT: 1-hydroxybenzotriazole
NMM: N-methyl morpholine
DCHA: Dicyclohexylamine
DCU: Dicyclohexylurea T.l.c. (Merck silica gel plates) with the solvent systems
SI: n-butanol/acetic acid/water (3:1:1) (by vol.)
SII: methylethylketone
SIII: chloroform/methanol/32% aq. acetic acid (120:90:5) (by vol.)
SIV: chloroform/methanol (8:1) (by vol.)
SV: chloroform/methanol/0.880 ammonia (120:90:5) (by vol.)
SVI: chloroform/methanol/32% aq. acetic acid (120:90:40) (by vol.)

SVII: chloroform/methanol/0.880 ammonia (120:90:40) (by vol.)

H.p.l.c.

Column: Zorbax C-8, 4.6 mm i.d. ×25 cm
Mobile phase: acetonitrile/0.1M ammonium acetate, pH 4.0
Flow rate: 2 ml/min
Detection: 254 nm.

The common intermediate protected dipeptide BOC-Tyr-D-Arg.HCl was synthesised as illustrated in Scheme I.

Scheme I:

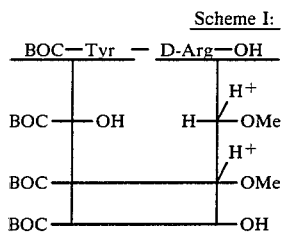

(A) BOC-Tyr-D-Arg-OMe

To BOC-Tyr[1] (1.184 g) in THF (20 ml) was added NMM (0.426 g) in THF (5 ml). The mixture was cooled to −25° C. and treated with isobutylchloroformate (0.549 g) in THF (5 ml) and allowed to react at −15° C. for 2 minutes. A precooled solution of D-Arg-OMe.2HCl[2] (1.0 g) and NMM (0.387 g) in DMF (20 ml) and water (2 ml) was added and the mixture was stirred at −15° C. for 2.5 hours. 2M KHCO$_3$ (4.6 ml) added and stirred at 0° C. for 30 min. Solvents were removed in vacuo, and the residue distributed between ethyl acetate and water. The organic phase was washed twice with water. The combined aqueous extracts were adjusted to pH 7 by the addition of acetic acid and after saturation with salt, extracted with chloroform/butanol 5:1 and then twice with chloroform. The combined organic layers were washed twice with sat. salt solution, dried (MgSO$_4$) and concentrated in vacuo. The residue was triturated with dry ether.

Yield 1.28 g (74%).

(B) BOC-Tyr-D-Arg.HCl

The protected dipeptide (1.28 g) was dissolved in methanol (40 ml) and water (10 ml). M NaOH (5.7 ml) was added and the mixture stirred at room temperature for 3½ hours, then neutralised by the addition of M HCl (5.7 ml). The methanol was removed in vacuo and the residual aqueous solution was freeze dried.

A solution of the crude product in water was desalted by absorption onto a Zorbax C-8 column and subsequent elution using a methanol gradient. The isolated dipeptide was dissolved in water, treated with one equivalent of M HCl and freeze dried.

Yield 0.78 g (58%).

Calc. for C$_{20}$H$_{31}$N$_5$O$_6$.HCl.2H$_2$O: C, 48.83; H, 6.91; N, 14.24. Found: C, 49.06; H, 6.79; N, 13.73%.

Single spot on T.l.c. in SI, SIII, SV.

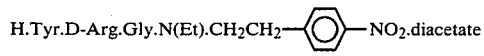

(EXAMPLE 1)

Scheme 2:

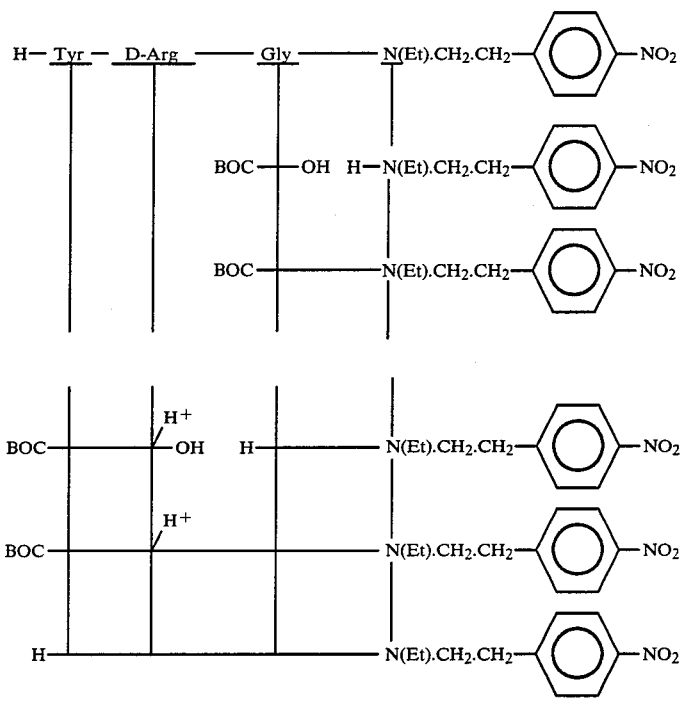

(A) 2-(4-Nitrophenyl)ethyl ethylamine hydrobromide

1-Bromo-2-(4-nitrophenyl)ethane (Aldrich, 10 g, 50 mmol) was stirred overnight at ambient temperature with a solution of ethylamine in ethanol (33%, 25 ml, ∼180 mmol). The orange solution was evaporated to leave a crystalline residue. The solid material was collected with the aid of ethanol (10 ml). Concentration of the filtrate yielded a second batch of product, identical on t.l.c., which was combined with the first.

Yield 5 g (36%), m.p. 211°–213° C.

The product was purified by recrystallisation from ethanol-ether.

Yield 4.25 g, m.p. 212°–214° C. T.l.c. homogeneous SIII, SV.

$C_{10}H_{15}N_2O_2Br$ requires: C, 43.65; H, 5.50; N, 10.18; Br, 29.04. found: C, 43.88; H, 5.73; N, 10.19; Br, 28.82%.

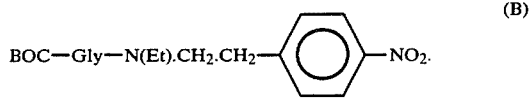

(B)

A solution of BOC-Gly[1] (3.89 g) and HOBT (6.00 g) in DMF (50 ml) was cooled to −10° C. and treated with DCCl (4.58 g). The reaction was stirred at −5° C. for 30 min prior to the addition of 4-nitrophenethyl ethylamine hydrobromide (4.08 g) and NMM (1.50 g). The mixture was stirred at 5° C. for 72 hr. Dicyclohexylurea was removed by filtration and the filtrate was concentrated. The residue was taken up in ethyl acetate and washed 3×5% $Na_2CO_3$ solution, 1× water, 2×5% citric acid solution and 2× water. The ethyl acetate extract was dried ($MgSO_4$) and evaporated in vacuo. The oil thus obtained was dissolved in ether, filtered from some dicyclohexylurea and re-evaporated to yield an oil (4.76 g) which could not be solidified by trituration under petrol.

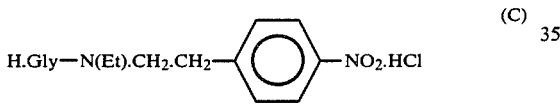

(C)

The protected amide (4.76 g) was dissolved in glacial acetic acid (35 ml) and treated with 2M HCl/acetic acid (35 ml) for 45 min at room temperature. Concentration in vacuo and trituration with dry ether yielded a solid product.

Yield 3.66 g (94%), m.p. 191°–194° C.

Calculated for $C_{12}H_{18}N_3O_3Cl$: C, 50.09; H, 6.26; N, 14.61. Found: C, 49.85; H, 6.38; N, 14.56%.

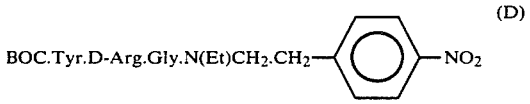

(D)

To a solution of BOC.Tyr.D-Arg.HCl (1.97 g) in DMF (20 ml) was added HOBT (1.13 g). The solution was cooled to −10° C. and DCCl (0.86 g) added.

The mixture was held at −5° C. for 30 min and then a solution of

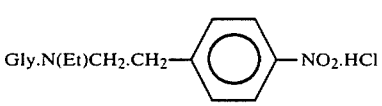

(1.2 g) and NMM (0.42 g) in DMF (5 ml) was added. The reaction mixture was stirred at 5° C. for 72 hours. Dicyclohexyl urea was filtered off and the filtrate concentrated in vacuo. The crude product was distributed between ethyl acetate (150 ml) and water (25 ml). The organic phase was extracted 5× with water and the combined aqueous extracts were shaken with 3×200 ml of ethyl acetate/n-butanol 5:1. The ethyl acetate/butanol extracts were washed with 3×150 ml 5% $Na_2CO_3$, 2×100 ml 5% citric acid and 2×100 ml water, concentrated in vacuo and re-evaporated twice from water and twice from ethanol. The resulting foam was triturated with ether.

T.l.c.: main spot reacts with Pauly reagent (tyrosine) and Sakaguchi reagent (arginine).

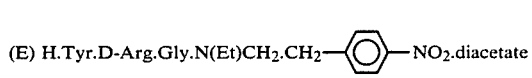

(E) H.Tyr.D-Arg.Gly.N(Et)CH₂.CH₂—⟨O⟩—NO₂.diacetate

The protected tripeptide amide (1.90 g) was dissolved in a mixture of glacial acetic acid (15 ml) and anisole (7.5 ml). This solution was treated wirh 2M HCl/acetic acid (22.5 ml) at room temperature for 30 min. Concentration in vacuo and trituration with dry ether yielded the crude product which was dissolved in water (20 ml) and washed twice with ether to remove residual anisole. The aqueous solution was applied to a 5×50 cm column of carboxymethyl cellulose and eluted with a linear gradient of ammonium acetate, pH 5.1. The main peak was desalted on a C-18 silica column to yield the peptide product.

Pure by analytical h.p.l.c and t.l.c (SI, SVI, SVII)

Calculated for $C_{27}H_{38}N_8O_6.2CH_3CO_2H.H_2O$: C, 52.54; H, 6.78; N, 15.82. Found: C, 52.74; H, 7.06; N, 15.58%.

$[\alpha]_D^{26} +32.1°$
$[\alpha]_{546}^{26} +37.9$ } (c = 1, MeOH)

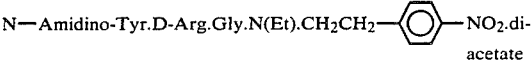

N—Amidino-Tyr.D-Arg.Gly.N(Et).CH₂CH₂—⟨O⟩—NO₂.diacetate (EXAMPLE 2)

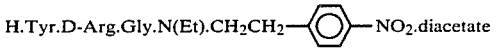

H.Tyr.D-Arg.Gly.N(Et).CH₂CH₂—⟨O⟩—NO₂.diacetate (708 mg) was dissolved in a mixture of ethanol (4 ml) and DMF (1 ml). 1-Amidino-3,5-dimethylpyrazole acetate (246 mg) and triethylamine (0.2 ml) were added. The mixture was stirred at 55° C. for 7 hr and then at room temperature overnight. Removal of solvents in vacuo and trituration with ethyl acetate, yielded a crude product which was purified by chromatography on a column of carboxymethylcellulose. Elution was by a linear gradient of ammonium acetate at pH 5.1 (0.005M→0.5M). Fractions containing the product were combined and freeze-dried three times to remove the volatile buffer.

TLC (Sl, SVI, SVII) indicated one major component. HPLC (30% acetonitrile) showed the presence of a single peak.

Calculated for $C_{28}H_{40}N_{10}O_6.2CH_3CO_2H.1.5H_2O$: C, 50.59; H, 6.72; N, 18.44. Found: C, 50.52; H, 6.72; N, 18.36%.

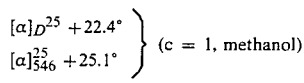
(c = 1, methanol)

H.Tyr.D-Arg.Gly.Et Phe(4NO₂).NH₂.diacetate
(EXAMPLE 3)

Scheme 3:

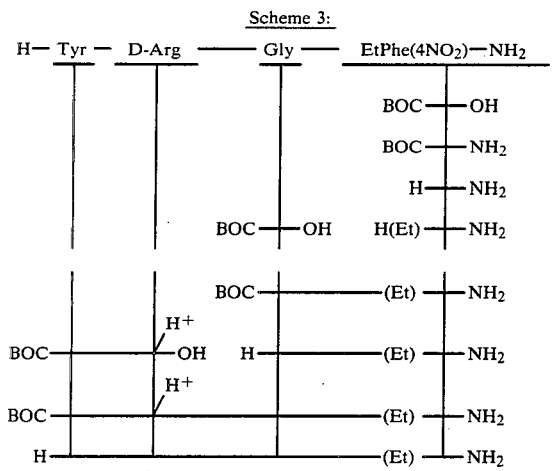

(A) BOC-Phe(4NO₂).NH₂

BOC-Phe(4NO₂)[3] (19.33 g) was dissolved in DMF and cooled to −15° C. NMM (6.30 g) and isobutylchloroformate (8.51 g) were added and the mixture was stirred for 5 min at −15° C. Ammonia was bubbled through the solution for 1 hr and the temperature was maintained at −15° C. for a further 1 hour. Nitrogen was bubbled through the reaction mixture to remove excess ammonia and then the solvent was removed in vacuo to yield a solid which was distributed between ethyl acetate and water. The organic phase was washed with 5% citric acid solution, water, 5% NaHCO₃ and finally water. After drying over anhydrous MgSO₄ and evaporation the residual solid was triturated with ethyl acetate/petrol to yield 16.94 g (88%).

Pure by t.l.c. (SI, SIII, SV).

Calculated for $C_{14}H_{19}N_3O_5$: C, 54.37; H, 6.15; N, 13.59. Found: C, 54.44; H, 6.12; N, 13.35%.

(B) H.Phe(4NO₂).NH₂.HCl

BOC-Phe(4NO₂).NH₂ (16.9 g) was suspended in anisole (150 ml) and treated with M HCl/acetic acid (500 ml). After 30 min at room temperature the mixture was concentrated in vacuo at 35° and the residue was triturated with dry ether.

Yield 13.6 g.

Pure by t.l.c. (SI, SIII, SV).

(C) H.Et Phe(4NO₂).NH₂

H.Phe(4NO₂).NH₂.HCl (13.6 g) was suspended in ethanol (200 ml) and treated with NaHCO₃ (18.7 g). The stirred suspension was heated to reflux and ethyl iodide (4.45 ml) was added. After refluxing for 5 hr the mixture was cooled and filtered. The filtrate was concentrated to an oil which solidified on trituration with petrol. This material was purified by dry column chromatography on silica gel, eluting with 5% methanol in dichloromethane.

Yield of purified material=2.75 g

(D) BOC-Gly.Et Phe(4NO₂).NH₂

BOC-Gly[1] (2.03 g) and HOBT (3.13 g) were dissolved in DMF (20 ml) and the solution was cooled to −10° C. DCCI (2.39 g) was added and the mixture was allowed to react at −10° C. for 30 min, before the addition of a solution of N.Et Phe(4NO₂).NH₂ in DMF. The reaction mixture was stirred at 5° C. overnight and then further quantities of BOC-Gly (2.03 g) and of DCCI (2.39 g) were added. The reaction was then allowed to proceed at room temperature for 48 hr. Dicyclohexylurea was filtered off and the filtrate was concentrated in vacuo to give an oil which was dissolved in ethyl acetate, filtered from dicyclohexylurea and washed with 2×5% NaHCO₃ and 1× water. After drying and removal of solvent 4.41 g (96%) of amorphous solid was obtained.

T.l.c. (SI, SIII, SV) showed the presence of some dicyclohexyl urea in the product.

(E) H.Gly.Et Phe(4NO₂).NH₂.HCl

The protected dipeptide amide (4.4 g) was dissolved in anisole (20 ml) and treated with M HCl/acetic acid (60 ml). After 30 min at room temperature the mixture was concentrated and the residue triturated with dry ether.

Yield 3.69 g (100%).

(F) BOC-Tyr.D-Arg.Gly.Et Phe(4NO₂).NH₂

BOC-Tyr.D-Arg.HCl (1.77 g), HOBT (0.98 g) and Gly.Et Phe(4NO₂).NH₂.HCl (1.20 g) were dissolved in DMF (30 ml) and the solution cooled to −10° C. DCCI (0.75 g) and NMM (0.37 g) were added and the mixture was stirred at 5° C. for 72 h. After filtering and evaporation the residual oil was distributed between ethyl acetate/n-butanol (5:1) and 5% NaHCO₃ solution saturated with NaCl. The organic phase was washed once with the above mixture and concentrated in vacuo. Re-evaporation from water (2×) and ethanol (2×) yielded the crude product which was carried to the next stage without further purification.

(G) H.Tyr.D-Arg.Gly.Et Phe(4NO₂).NH₂.diacetate

The protected tetrapeptide amide (2.13 g) was treated with anisole (10 ml) and M HCl/acetic acid (100 ml) at room temperature for 40 min. Evaporation and trituration with dry ether yielded the crude product. This was applied to a 5×50 cm column of carboxymethyl cellulose and eluted using a linear gradient of ammonium acetate at pH 5.1. Fractions containing the pure product were combined and freeze-dried three times.

Pure by t.l.c. (SI, SVI, SVII) and analytical h.p.l.c.

Calculated for $C_{32}H_{47}N_9O_{11}.2H_2O$: C, 49.93; H, 6.63; N, 16.38. Found: C, 50.18; H, 6.35; N, 16.33%

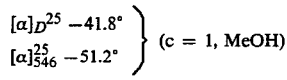
(c = 1, MeOH)

References
1. *J.A.C.S.*, 79, 6180 (1957).
2. *Helv. Chim. Acta*, 41, 1867 (1958)

3. J. Chem. Soc. Japan, 62, 31 (1941)
Khim. Prir. Soedin, (1979), 543.

N-Amidino-Tyr.D-Arg.Gly.Et Phe(4NO₂).NH₂,diacetate (EXAMPLE 4)

Ex. 19. Calc: C, 51.88; H, 6.83; N, 15.34. Found: C, 51.50; H, 6.69; N, 15.75.

Ex. 20. Calc: C, 54.62; H, 7.05; N, 14.39. Found: C, 54.80; H, 6.99; N, 14.50.

Ex. 28. Calc: C, 47.88; H, 6.40; N, 13.96. Found: C, 47.68; H, 6.48; N, 14.08.

| Example | R¹ | X² | R² | R³ | n | Z¹ | Z² | $[\alpha]_D^{25}$ (c = 1, methanol) | $[\alpha]_{546}^{25}$ (c = 1, methanol) |
|---|---|---|---|---|---|---|---|---|---|
| 5 | H | D-Arg | C₂H₅ | H | 1 | 4-F | H | +35.0° | +40.6° |
| 6 | H | D-Arg | C₂H₅ | H | 2 | 4-NO₂ | H | | |
| 7 | H₂NC(:HN) | D-Arg | C₂H₅ | H | 1 | 4-F | H | | |
| 8 | H | D-Arg | C₂H₅ | H | 0 | 4-NO₂ | H | +34.8° | +41.1° |
| 9 | H₂NC(:HN) | D-Arg | C₂H₅ | H | 0 | 4-NO₂ | H | +26.4° | +31.7° |
| 10 | H | D-Arg | C₂H₅ | H | 0 | 4-F | H | +37.4° | +44.3° |
| 11 | H | D-Arg | C₂H₅ | CONH₂ | 1 | 4-CF₃ | H | −27.7° | −32.7° |
| 12 | H | D-Arg | CH₃ | CONH₂ | 1 | 4-NO₂ | H | +32.0° | +37.6° |
| 13 | H | D-Arg | C₂H₅ | CONH₂ | 1 | 4-F | H | −7.5° | −9.0° |
| 14 | H | D-Arg | C₂H₅ | CONH₂ | 1 | 2-F | H | −11.1° | −13.7° |
| 15 | H | D-Arg | C₂H₅ | CONH₂ | 1 | 3-F | H | −3.9° | −4.6° |
| 16 | H | D-Arg | C₂H₅ | CONH₂ | 1 | 4-Cl | H | −31.1° | −38.1° |
| 17 | H | D-Arg | C₂H₅ | H | 0 | 2-NO₂ | H | +36.3° | +44.2° |
| 18 | H | D-Arg | C₂H₅ | H | 0 | 2-F | H | +38.7° | +42.7° |
| 19 | H | D-Arg | C₂H₅ | H | 1 | 2-NO₂ | H | | |
| 20 | H | D-Arg | C₂H₅ | H | 1 | 2-F | H | | |
| 21 | H₂NC(:HN) | D-Arg | C₂H₅ | H | 0 | 2-NO₂ | H | +26.6° | +33.0° |
| 22 | H₂NC(:NH) | D-Arg | C₂H₅ | H | 0 | 2-F | H | +25.8° | +30.6° |
| 23 | H₂NC(:NH) | D-Arg | C₂H₅ | H | 1 | 2-NO₂ | H | +17.0° | +24.6° |
| 24 | H₂NC(:HN) | D-Arg | C₂H₅ | H | 1 | 2-F | H | +20.7° | +27.6° |
| 25 | CH₃ | D-Arg | C₂H₅ | H | 1 | 4-NO₂ | H | +32.8° | +39.1° |
| 26 | H | D-Arg | C₂H₅ | H | 1 | 4-NO₂ | 2-NO₂ | +27.1° | +31.8° |
| 27 | H₂NC(:HN) | D-Arg | C₂H₅ | H | 1 | 4-NO₂ | 2-NO₂ | +22.2° | +26.2° |
| 28 | H | D-Arg | C₂H₅ | CONH₂ | 1 | 4-Cl | 3-Cl | | |
| 29 | H | D-Arg | C₂H₅ | H | 1 | 4-Cl | 3-Cl | +33.3° | +39.2° |
| 30 | H₂NC(:HN) | D-Arg | C₂H₅ | H | 1 | 4-Cl | 3-Cl | +23.7° | +26.9° |
| 31 | H | D-Arg | C₂H₅ | H | 1 | 4-Br | H | +31.4° | +38.8° |
| 32 | H₂NC(:HN) | D-Arg | C₂H₅ | H | 1 | 4-Br | H | +22.9° | +31.2° |
| 33 | H₂NC(:HN) | D-Arg | C₂H₅ | CONH₂ | 1 | 4-F | H | −12.8° | −14.3° |

H.Tyr.D-Arg.Gly.Et Phe(4NO₂).NH₂.diacetate (321 mg) was dissolved in ethanol (2 ml) and DMF (0.5 ml). 1-Amidino-3,5-dimethylpyrazole acetate (108 mg) and triethylamine (0.09 ml) were added and the mixture was stirred at 55° C. for 5 hr and then at room temperature overnight. The crude product obtained after removal of solvents was applied to a column of carboxymethylcellulose and eluted by means of a linear gradient of ammonium acetate, pH 5.1 (0.005M→0.5M). Isolation of the purified peptide by repeated freeze-drying yielded material which was pure by TLC (SI, SVI) and HPLC (30% acetonitrile).

Calculated for C₂₉H₄₁N₁₁O₇.2CH₃CO₂H.2.5H₂O: C, 48.29; H, 6.58; N, 18.78. C, 47.92; H, 6.28; N, 18.61%.

$[\alpha]_D^{25}$ −44.2°  
$[\alpha]_{546}^{25}$ −53.6°  } (c = 1, methanol)

The following further peptides were prepared by methods standard in peptide chemistry and similar to those described in the foregoing Examples. All compounds were isolated and characterised as the diacetate addition salt unless otherwise stated.

The elemental analyses for those compounds for which no optical rotation figures are shown were as follows:

Ex. 6. Calc: C, 53.17; H, 6.97; N, 15.50. Found: C, 53.03; H, 6.89; N, 15.58.

Ex. 7. Calc: C, 51.81; H, 7.06; N, 16.99. Found: C, 52.00; H, 6.76; N, 17.06.

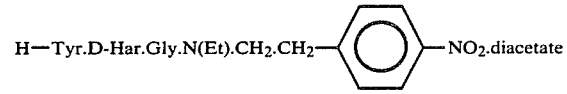

(EXAMPLE 34)

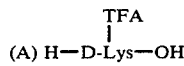

D-Lysine hydrochloride (10 g) was dissolved in M NaOH solution (55 ml) and treated with s-ethyl trifluorothioacetate (11 ml). The mixture was stirred vigorously at room temperature for 7 hr in a slow stream of nitrogen. After standing at room temperature overnight, the mixture was cooled in ice and the product filtered off and washed with a small volume of cold water and then ethanol. Dried over P₂O₅.

Yield 4.5 g

Single spot on T.l.c. in S1, S111.

Calculated for C₈H₁₃N₂O₃F₃: C, 39.67; H, 5.41; N, 11.57. Found: C, 39.69; H, 5.55; N, 11.43.

TFA stands for the trifluoroacetyl group.

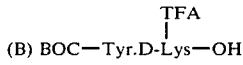

BOC-Tyr-OH (5.11 g) and N-hydroxysuccinimide (2.09 g) were dissolved in a mixture of dioxan (20 ml), ethyl acetate (5 ml) and DMF (10 ml). The solution was cooled to −5° C. and treated with DCCl (3.75 g). The mixture was stirred at −5° C. for 1 hr and then allowed to warm to R.T. over 1 hr. DCU was removed by filtration and washed with ethyl acetate. The combined filtrate was cooled in ice and treated with a solution of

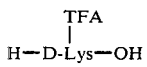
H—D-Lys—OH
TFA (above the Lys)

(4.4 g) and NaHCO₃ (3.06 g) in H₂O (90 ml) and DMF (15 ml). The reaction mixture was stirred at R.T. overnight, filtered and concentrated in vacuo to remove volatile organic solvents. The resulting aqueous DMF solution was diluted with water and adjusted to pH 3.5 by the addition of solid citric acid. The product was extracted with ethyl acetate (1×150 ml, 2×75 ml) and the combined organic extracts were washed with 5% citric acid (50 ml) and water (2×50 ml), dried over anhyd. MgSO₄ and concentrated to yield an oil (10.6 g) which was not characterised.

(C) BOC-Tyr-D-Lys-OH

The product from the previous step was dissolved in methanol (56 ml) and treated with M NaOH (56 ml). After 20 hr at room temperature, the pH was adjusted to 7.0 by the addition of M HCl and methanol was removed in vacuo. The resulting solution was diluted to 250 ml with water and acidified to pH 4.0 with M HCl. Unreacted starting material was washed out with ethyl acetate (3×100 ml) and the product was isolated by absorption onto a 2.5×50 cm column of C18-silica, elution with water to remove salt and then elution with methanol. The methanol eluate was concentrated and the resulting residue was dissolved in water and freeze dried.

Yield 5.21 g

Pure by T.l.c. in S111.

Calculated for C₂₀H₃₁N₃O₆1.5H₂O: C, 55.04; H, 7.80; N, 9.63. Found: C, 55.02; H, 7.64; N, 9.73.

(D) BOC-Tyr.D-Har-OH.HCl

A solution of BOC-Tyr.D-Lys-OH (3.5 g) in ethanol (20 ml) was treated with 1-amidino-3,5-dimethyl pyrazole acetate (2.11 g) and triethylamine (1.7 ml). The mixture was maintained at 65° C. for 7.5 hr and then stood at R.T. overnight. After removal of solvent, the residue was distributed between 4% acetic acid (25 ml) and ethyl acetate (25 ml). The aqueous phase was separated, washed again with ethyl acetate (20 ml) and applied to a 5×47 cm column of carboxymethyl cellulose. Gradient elution from 0.005M to 0.1M ammonium acetate, pH 5.1 and subsequent freeze drying yielded 3.6 g crude product. This material was purified further by reversedphase chromatography on C8-silica and finally converted to the hydrochloride.

Yield 2.86 g

T.l.c: one major component in S1, S111

Calculated for C₂₁H₃₄N₅O₆Cl.H₂O: C, 49.85; H, 7.12; N, 13.85. Found: C, 49.69; H, 7.02; N, 14.06.

(E) BOC—Tyr.D-Har.Gly.N(Et).CH₂.CH₂— 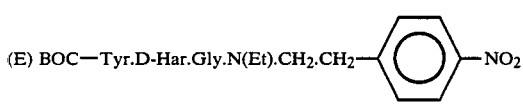 —NO₂

BOC-Tyr.D-Har-OH.HCl (487.5 mg) and HOBT (270 mg) were dissolved in DMF (10 ml). The solution was cooled to −5° C. and treated with DCCI (206 mg). The mixture was maintained at 0° C. for 30 min, then treated with Gly.N(Et).CH₂.CH₂— 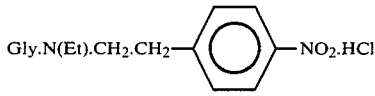 —NO₂.HCl (287.5 mg) and NMM (101 mg), and stirred at +5° C. for 72 hr. After the removal of DCU and concentration in vacuo, the residue was distributed between 5% citric acid solution (75 ml) and ethyl acetate (50 ml). The separated aqueous layer was washed with ethyl acetate (2×50 ml) and adjusted to pH 6.0 by addition of solid K₂CO₃. The product was extracted into ethyl acetate/n-butanol 4:1 (3×75 ml) and the combined extracts were evaporated to dryness and then re-evaporated from water (1×) and ethanol (3×) to yield a solid foam.

Yield 800 mg

T.l.c: one major component in S1, S111

(F) H—Tyr.D-Har.Gly.N(Et).CH₂.CH₂—  —NO₂, diacetate

The protected peptide (800 mg) was dissolved in a mixture of anisole (5 ml) and acetic acid (10 ml) and treated with 2M HCl in acetic acid (10 ml). After 30 min at room temperature the solvents were removed in vacuo and the resulting residue was dissolved in water and washed with ether. The crude product was purified by ion-exchange chromatography on carboxymethyl cellulose.

T.l.c: pure in S1, SVI

Calculated for C₂₈H₄₀N₈O₆.2CH₃CO₂H.0.5H₂O: C, 53.86; H, 6.87; N, 15.71. Found: C, 53.59; H, 6.98; N, 15.92.

$[\alpha]_D^{25}$ +36.6°
$[\alpha]_{546}^{25}$ +44.6°   (c = 1, methanol)

N—Amidino-Tyr.D-Har.Gly.N(Et).CH₂.CH₂— 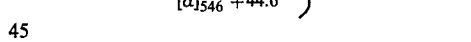 —NO₂, diacetate (EXAMPLE 35)

A solution of

Tyr.D-Har.Gly.N(Et).CH₂.CH₂— 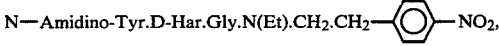 —NO₂, diacetate (263 mg) in ethanol (2 ml) was treated with 1-amidino-3,5-dimethyl pyrazole acetate (115 mg) and triethylamine (0.1 ml) for a total of 10 hr at 60° C. After removal of ethanol the crude product was distributed between H₂O and ethyl acetate. The aqueous solution was purified on a column of carboxymethyl cellulose (2.5×45 cm).

T.l.c: pure in S1, SV1, SV11

Calculated for $C_{29}H_{42}N_{10}O_6.2CH_3CO_2H.2.5H_2O$: C, 50.56; H, 6.95; N, 17.70. Found: C, 50.21; H, 6.72; N, 17.65.

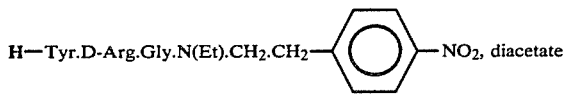

(EXAMPLE 36)

(A) BOC-Tyr.D-Arg.Gly.OBzl.CHI

A solution of BOC-Tyr.D-Arg.OH.HCl (1.42 g), HOBT (0.81 g), H-Gly-OBzl, toluene sulphonate (1.06 g) and NMM (0.303 g) in DMF (15 ml) was cooled to −5° C. and treated with DCCI (0.618 g). The mixture was stirred at 4° C. for 24 hr, then filtered and the filtrate concentrated in vacuo. The residue was distributed between ethyl acetate (100 ml) and ice-cold M HCl (100 ml). The aqueous layer was extracted with ethyl acetate (1×100 ml, 2×50 ml) and the combined organic extracts were washed with 5% $NaHCO_3$ (3×50 ml) and saturated NaCl (1×50 ml), dried and evaporated to yield an amorphous solid.

Yield 1.44 g

Not characterised. T.L.C. indicated the presence of DCU.

(B) BOC-Tyr.D-Arg.Gly-OH.HCl

The benzyl ether (1.44 g) was dissolved in methanol (50 ml) and hydrogenated in the presence of 10% palladium charcoal catalyst (140 mg). After 4 hr the catalyst was removed by filtration, the solvent was evaporated in vacuo and the product triturated with ether.

Yield 1.15 g

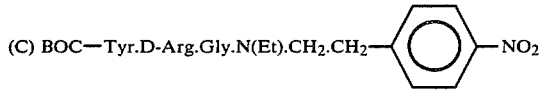

BOC-Tyr.D-Arg.Gly.OH.HCl (530.5 mg), HOBT (270 mg),

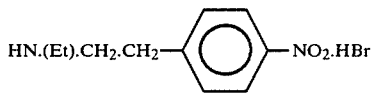

(275 mg) and $Et_3N$ (101 mg) were dissolved in DMF (10 ml). The solution was cooled to −5° C. and treated with DCCI (206 mg). The mixture was stirred at 5° C. for 72 hr. and worked up as previously described.

Yield 640 mg

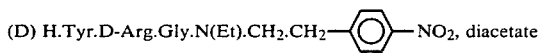

The protected peptide (640 mg) was dissolved in a mixture of anisole (11 ml) and acetic acid (16 ml) and treated with 2M HCl in acetic acid (16 ml). After 30 min. at room temperature the reaction mixture was concentrated in vacuo and the residue was distributed between water and ether. The crude product was isolated from the aqueous layer by freeze-drying and purified by ion-exchange chromatography on carboxymethyl cellulose.

T.l.c: pure in S1

H.P.L.C. profile identical to that of product isolated by alternative route.

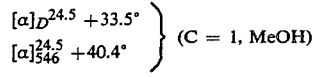

$[\alpha]_D^{24.5}$ +33.5°
$[\alpha]_{546}^{24.5}$ +40.4°  } (C = 1, MeOH)

Calculated for $C_{27}H_{38}N_8O_6.2CH_3CO_2H_2H.H_2O$: C, 52.54; H, 6.78; N, 15.82. Found: C, 52.46; H, 7.32; N, 16.08.

H-Tyr.D-Arg.Gly.Et Phe(4NO$_2$).NH$_2$, diacetate (EXAMPLE 37)

(A) H-Et Phe(4NO$_2$)-OH.HCl

H-Et Phe(4NO$_2$).NH$_2$ (5 g) was heated to reflux in 6M HCl (100 ml) for 4 hr. The pale yellow solution was cooled and refrigerated overnight to yield 4.6 g of product as off-white needles, which melted with decomposition at 272°–275° C.

Calculated for $C_{11}H_{15}N_2O_4Cl$: C, 48.09; H, 5.46; N, 10.20. Found: C, 48.22; H, 5.47; N, 10.20.

(B) H-Et Phe(4NO$_2$)-OMe.HCl

Methanol (50 ml) was trated with thionyl chloride (2 g) at −15° C. and then H-Et Phe(4NO$_2$)-OH.HCl (4.12 g) was added. The mixture was stirred at 20° C. for 2 hr and then refluxed for a total of 24 hr. The solvent was removed in vacuo and the crude product crystallised from MeOH (40 ml) and ether (40 ml).

Yield 3.4 g (C) BOC-Gly.Et Phe(4NO$_2$)-OMe

BOC-Gly (3.0 g) and HOBT (3.5 g) were dissolved in DMF (20 ml). The solution was cooled in ice and treated with DCCI (3.3 g). After 30 min, a solution of H-Et Phe(4NO$_2$)-OMe.HCl (3.3 g) and NMM (1.27 g) in DMF (30 ml) and H$_2$O (1 ml) was added and the reaction mixture was stirred at 0° C. for 1 hr and then at room temperature overnight. T.l.c. indicated that the reaction was not complete. A further quantity of DCCI (1.18 g) was added and the mixture was stirred for an additional 24 hr. DCU was filtered off and the DMF was evaporated in vacuo. The residue was taken up in ethyl acetate and refrigerated for 2 hr. DCU was removed by filtration and the ethyl acetate solution was washed with 5% NaHCO$_3$ (4×), 10% citric acid (2×), water (2×) and brine (1×). The solution was dried and concentrated to yield 2.69 g of an oil which was used in the next stage without further purification. T.l.c. showed the presence of some DCU.

(D) H-Gly.Et Phe(4NO$_2$)-OMe.HCl

The protected dipeptide (2.3 g) was treated with 1M HCl in acetic acid (33 ml) for 1 hr at room temperature. The residue obtained after concentration in vacuo was dissolved in water, washed with ether (3×) and freeze dried.

Yield 1.42 g (E) BOC-Tyr.D-Arg.Gly.Et Phe(4NO$_2$)-OMe

A solution of BOC-Tyr.D-Arg.HCl (1.96 g) and HOBT (1.11 g) in DMF (17 ml) was cooled in ice and treated with DCCI (0.93 g). The mixture was stirred at 0° C. for 1 hr and then treated with a solution of H-Gly.Et Phe(4NO₂)-OMe.HCl (1.42 g) and NMM (0.42 g) in DMF (17 ml). After 24 hr at room temperature a further quantity of DCCI (0.42 g) was added and the mixture was stirred for a further 24 hr. The usual work-up procedure yielded 3.6 g of product.

(F) H-Tyr.D-Arg.Gly.Et Phe(4NO₂)-OMe, diacetate

The protected tetrapeptide methyl ester (3.6 g) was deprotected in the usual way and purified by chromatography on carboxymethylcellulose.
Yield 1.55 g
Calculated for $C_{29}H_{40}N_8O_8,2CH_3CO_2H,1.5H_2O$: C, 51.09; H, 6.62; N, 14.44. Found: C, 51.15; H, 6.44; N, 14.70.

(G) H-Tyr.D-Arg.Gly.Et Phe(4NO₂)-NH₂, diacetate

The tetrapeptide methyl ester (0.5 g) was dissolved in methanol (25 ml). The solution was cooled in ice and saturated with anhydrous ammonia. The flask was sealed and maintained at R.T. for 24 hr. T.l.c. indicated complete reaction. Excess ammonia and methanol were removed by evaporation to yield the crude product which was purified by ion-exchange chromatography on carboxymethyl cellulose. Product was identical by T.l.c. and HPLC to that prepared by the alternative route.
Calculated for $C_{28}H_{39}N_9O_7,2CH_3CO_2H,1H_2O$: C, 51.13; H, 6.52; N, 16.78. Found: C, 51.21; H, 6.43; N, 17.06.

PHARMACOLOGICAL RESULTS

(A) Hotplate test

Male mice (CFLP strain, Hacking and Churchill) were individually placed in a copper-bottomed perspex box suspended in a water bath at 55° C. and observed for signs of discomfort such as shaking or licking the paws, the reaction time (up to a maximum of 30 secs.) being recorded. Groups of five animals then received either a test compound or saline vehicle (0.85%) control by subcutaneous injection, the test being repeated at 15 mins. after treatment. The $ED_{50}$ figures for the test compounds were calculated from the number of animals having a posttreatment reaction time which was twice the pretreatment figure.

(B) Irritant-induced writhing test (i) Acetic Acid. Groups of five female CD1 mice (Charles River) received either a test compound or saline vehicle (0.85%) control by subcutaneous injection 15 mins. prior to an intraperitoneal injection of 0.6% acetic acid at a dose volume of 25 ml/kg. After a further 20 mins. the writhing or stretching movements induced by the irritant were counted over a 2½ min. period, a writhe/stretch being identified as an extension of a hindlimb accompanied by constriction of the abdomen.

(ii) Phenylbenzoquinone (PBQ). This test was carried out in a parallel manner to that employing acetic acid, except that the period over which the writhing/stretching movements were counted began 10 mins. after administration of the PBQ irritant, the latter being given at a dosage of 2.5 mg/kg and in a dose volume of 10 ml/kg. The $ED_{50}$ figures for the test compounds were calculated, using linear regression analysis, as the dose in the presence of which only half the number of writhes/stretches was induced compared with the controls.

(C) Antagonism by quaternary opioid

Groups of six male TFW mice (Tuck) received by intraperitoneal injection either N-methylnalorphine (16 mg/kg) or saline vehicle (0.85%) control at a volume of 10 ml/kg followed after 20 mins. by a solution of the test compound in saline (10 ml/kg, subcutaneous) and after a further 30 mins. by 0.6% acetic acid (25 ml/kg, intraperitoneal). The total number of writhes/stretches per group was then determined over the 5 min. period commencing 15 mins. after administration of the acetic acid. Using linear regression analysis the $ED_{50}$ figures for the test compounds were calculated (defined as in (B) supra) together with the dose ratios therefor, i.e. the ratios of the dose of compound required for equiactive antinociceptive effect in respectively the presence and the absence of the quaternary compound.

(D) Antitussive activity

In this test procedure, a modification of that described by Boura et al, Br. J. Pharmac., 39/1 (1970) 225, guinea pigs were subjected to an aerosol containing 30% citric acid, 30 minutes after subcutaneous administration of test compound as a solution in 0.85% (w/w) saline, and the number of coughs during a 12½-minute exposure counted. The

| Compound | (A) Hotplate | (B) Writhing Acetic acid | PBQ | (C) Writhing N—methyl-nalorphine (a) | Saline control (b) | Dose ratio (a):(b) | (D) Antitussive |
|---|---|---|---|---|---|---|---|
| Dextropropoxyphene | 25.9 | 4.2 | 2.6 | 6.9 | 6.8 | 1.0 | |
| Indomethacin | NE @ 100 | | 0.9 | | | | |
| Morphine | 1.8 | 0.45* | 0.38 p.o. 3.5* | 0.24 | 0.4 | 0.9 | |
| Pentazocine | NE @ 100 | 2.3 | | | | | |
| Ex. 1 | NE @ 100 | 14.0 p.o. 30.6* | 6.2 p.o. 43.5* | 12.5 | 2.8 | 4.5 | 3.0 |
| Ex. 2 | NE @ 50 | | 0.18 p.o. 10.0* | 1.2 | 0.12 | 9.6 | 0.06 |
| Ex. 3 | 1.0 p.o. 159.9** | 0.03 p.o. 0.9* | 0.02 p.o. 14.0* | 0.08 | 0.03 | 3.4 | 0.001 |
| Ex. 4 | 1.5 | 0.009* | 0.008 p.o. 1.9* | 0.007 | 0.001 | 5.1 | 0.01 |
| Ex. 33 | 1.5 p.o. NE | 0.008* | 0.08 p.o. 25.6* | 0.01 | 0.002 | 6.5 | 0.004 |

|          |              | (B) Writhing |     | (C) Writhing |         |           |               |
|----------|--------------|--------------|-----|--------------|---------|-----------|---------------|
|          |              |              |     | N—methyl-    | Saline  |           |               |
|          |              | Acetic       |     | nalorphine   | control | Dose ratio |              |
| Compound | (A) Hotplate | acid         | PBQ | (a)          | (b)     | (a):(b)   | (D) Antitussive |
|          | @ 100*       |              |     |              |         |           |               |

NE: no effect
p.o.: per os
*test compound administered 30 min. prior to acetic acid/PBQ
**test repeated at 30 min. after treatment ED$_{50}$ figures (the dose required to reduce the number of coughs by 50% compared with saline-treated controls) were calculated using linear regression analysis.

The results are set out in the accompanying table expressed as mg. compound/kg. bodyweight and, where appropriate, as the free peptide.

(E) Antidiarrhoeal activity

Female Cobs Wistar rats (Charles River) were starved for 24 hours prior to oral administration of the test compound as an aqueous solution at a volume of 10 ml/kg. Fifteen minutes after the compound each rat received 1 ml. castor oil given orally and the animals were then observed for the appearance of diarrhoea. The ED$_{50}$s for each compound, calculated as the dose (mg. of free peptide/kg. bodyweight) required to suppress diarrhoea in 50% of the animals, were derived from the results obtained at various intervals post castor oil.

| Compound | 1.0 hrs.* | 1.5 hrs* | 2.0 hrs* | 2.5 hrs* |
|----------|-----------|----------|----------|----------|
| Ex. 1    | 8.5       | 30.3     | 40.5     |          |
| Ex. 2    | 1.9       | 3.2      | 16.7     | 28.6     |
| Ex. 3    |           | 0.11     | 0.31     | 0.46     |
| Ex. 33   | 0.02      | 0.03     | 0.02     | 0.05     |

*post castor oil (F) Cardiovascular effects

The compound of Example 2, as a solution in 0.85% (w/w) saline, was administered to male Wistar rats (300–400 g) by intravenous bolus injection at a dose volume of 0.1 ml/100 g bodyweight. Over the dose range 0.01 to 1.0 mg/kg (calculated as the free peptide) a dose-dependent hypotension was seen associated with bradycardia.

(G) Toxicity

In the mouse the compound of Example 2 proved toxic to the following extent:
500 mg (base)/kg p.o.: 1/5 animals died
200 mg (base)/kg s.c.: 5/5 animals died

PHARMACEUTICAL FORMULATIONS

In the following the "Compound" is a salt of a peptide of formula (I) as hereinbefore defined, the weight thereof being calculated as the free peptide.

| (A) Capsule        |            |
|--------------------|------------|
| Compound           | 5.0 mg     |
| Magnesium stearate | 0.75 mg    |
| Lactose BP         | to 200.0 mg |

Mix the ingredients and fill into hard gelatin capsules, each to contain 5.0 mg of compound calculated as free peptide.

| (B) Tablet                            |             |
|---------------------------------------|-------------|
| Compound                              | 5.0 mg      |
| Avicel PH 101                         | 22.5 mg     |
| Low-substituted hydroxypropylcellulose | 9.0 mg      |
| Polyvinylpyrrolidone K30              | 6.0 mg      |
| Magnesium stearate                    | 0.75 mg     |
| Lactose BP                            | to 150.0 mg |

| (C) Freeze-Dried Injection |           |
|----------------------------|-----------|
| Compound                   | 5.0 mg    |
| Mannitol                   | 62.5 mg   |
| Water for Injections       | to 2.5 ml |

Dissolve the mannitol and compound in 9/10 the total quantity of water and make to volume when solution is complete. Under sterile conditions, sterilise the solution by filtration through a suitable, sterile, sterilising grade filter and pack into clean, sterile vials using a fill of 2.5 ml per vial. Partially insert freeze drying stoppers into the necks of the vials and freeze dry. Close the vials under an inert gas and secure with aluminium collars.

| (D) Suppository |              |
|-----------------|--------------|
| Compound        | 5.0 mg       |
| Hard Fat BP     | to 1000.0 mg |

| (E) Dermal Lotion        |            |
|--------------------------|------------|
| Compound                 | 0.4 g      |
| Sorbitan monolaurate     | 0.6 g      |
| Polysorbate 20           | 0.6 g      |
| Cetostearyl alcohol      | 1.2 g      |
| Glycerin                 | 6.0 g      |
| Methyl p-hydroxybenzoate | 0.2 g      |
| Purified Water BP        | to 100.0 ml |

Dissolve the methyl p-hydroxybenzoate and glycerin in 70 ml of the water at 75° C.; melt together the sorbitan monolaurate, polysorbate 20 and cetostearyl alcohol at 75° C. and add to the aqueous solution. Homogenise the resulting emulsion, allow to cool with continuous stirring and add the compound as a solution in the remaining water; stir the product until homogeneous.

What we claim is:

1. A peptide of formula (I)

$$R^1.Tyr.X^2.Gly.N-\underset{R^2}{\underset{|}{CH}}-(CH_2)_n-\underset{Z^2}{\overset{Z^1}{\bigcirc}} \qquad (I)$$

or a salt thereof wherein
R$^1$ is hydrogen, alkyl of 1 or 2 carbon atoms or an amidino group,
R$^2$ is alkyl of 1 or 2 carbon atoms, $R^3$ is hydrogen or carbamyl, $X^2$ is a D-radical having the structure:

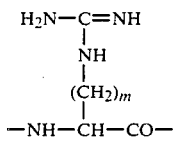

$Z^1$ and $Z^2$ are the same or different and each is hydrogen, halo, nitro or trifluoromethyl and at least one is other than hydrogen, m is 3 or 4 and n is 0, 1 or 2, provided that when $R^3$ is carbamyl then n is always 1.

2. A compound according to claim 1 wherein $R^1$ is an amidino group.

3. A compound according to claim 1 wherein $X^2$ is D-arginyl.

4. A compound according to claim 1 wherein $R^2$ is ethyl.

5. A compound according to claim 1 wherein $R^3$ is hydrogen.

6. A compound according to claim 1 wherein $R^3$ is carbamyl.

7. A compound according to claim 1 wherein n is 1.

8. A compound according to claim 1 wherein one of $Z^1$ and $Z^2$ is hydrogen and the other is nitro or fluoro.

9. A compound according to claim 1 wherein one of $Z^1$ and $Z^2$ is hydrogen and the other is in the 4-position.

10. The peptide having the structure

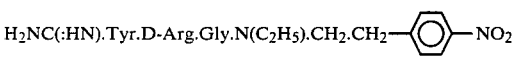

and salts thereof.

11. The peptide having the structure

and salts thereof.

12. The peptide having the structure

and salts thereof.

13. A salt of a peptide according to claim 1.

14. A pharmacologically acceptable salt of a peptide according to claim 1.

15. A pharmacologically acceptable salt of the peptide according to claim 10.

16. A pharmacologically acceptable salt of the peptide according to claim 11.

17. A pharmacologically acceptable salt of the peptide according to claim 12.

18. The diacetate salt of a peptide according to claim 1.

19. A pharmaceutical formulation for use in obtaining an effect selected from analgesic, anti-diarrhoeal, anti-dysentery and anti-tussive comprising a treatment effective amount of a peptide according to claim 1 or a pharmacologically acceptable salt thereof, together with an acceptable carrier therefor.

20. A formulation according to claim 19, suitable for oral administration.

21. A formulation according to claim 19, suitable for parenteral administration.

22. A formulation according to claim 19, suitable for rectal administration.

23. A formulation according to claim 19, suitable for topical administration.

24. A formulation according to claim 19 comprising a peptide salt in solution in an aqueous medium.

25. A formulation according to claim 19 in unit dosage form containing a non-toxic amount of the peptide or salt.

26. A formulation according to claim 25 in the form of a tablet suitable for oral administration.

27. A formulation according to claim 25 in the form of a capsule suitable for oral administration.

28. A formulation according to claim 25 in the form of a sterile injection solution suitable for parenteral administration.

29. A formulation according to claim 25 in the form of a suppository suitable for rectal administration.

30. A unit dosage formulation according to claim 25 containing from 0.5 to 50 mg of the peptide or salt, calculated as the free peptide.

31. A method for the relief or prevention of pain in a mammal comprising administering to said mammal a non-toxic, analgesic amount of a peptide according to claim 1 or a pharmacologically acceptable salt thereof.

32. A method for the treatment of diarrhoea or dysentery in a mammal comprising administering to said mammal a non-toxic, effective amount of a peptide according to claim 1 or a pharmacologically acceptable salt thereof.

33. A method for the suppression of cough in a mammal comprising administering to said mammal a non-toxic, effective amount of a peptide according to claim 1 or a pharmacologically acceptable salt thereof.

34. A method according to claim 31 wherein the mammal is a human being.

35. A method according to claim 32 wherein the mammal is a human being.

36. A method according to claim 33 wherein the mammal is a human being.

37. A formulation according to claim 19 comprising the peptide having the structure

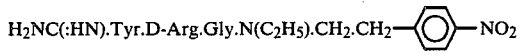

or a pharmacologically acceptable salt thereof, together with an acceptable carrier therefor.

38. A formulation according to claim 19 comprising the peptide having the structure

or a pharmacologically acceptable salt thereof, together with an acceptable carrier therefor.

39. A formulation according to claim 19 comprising the peptide having the structure

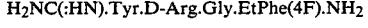

or a pharmacologically acceptable salt thereof, together with an acceptable carrier therefor.

40. A method according to claim 31, claim 32 or claim 33 which comprises administering to said mammal the peptide having the structure

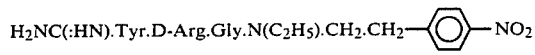

or a pharmacologically acceptable salt thereof.

41. A method according to claim 31, claim 32 or claim 33 which comprises administering to said mammal the peptide having the structure

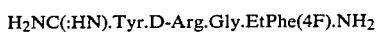

or a pharmacologically acceptable salt thereof.

42. A method according to claim 31, claim 32 or claim 33 which comprises administering to said mammal the peptide having the structure H₂NC(:HN).Tyr.D-Arg.Gly.EtPhe(4F).NH₂ or a pharmacologically acceptable salt thereof.

* * * * *